United States Patent
Cooke et al.

(10) Patent No.: US 9,189,940 B2
(45) Date of Patent: Nov. 17, 2015

(54) METHOD AND APPARATUS FOR DETECTING SMOKE IN AN ION CHAMBER

(71) Applicant: Microchip Technology Incorporated, Chandler, AZ (US)

(72) Inventors: Benjamin T. Cooke, Denver, CO (US); Joseph Julicher, Maricopa, AZ (US); Keith Edwin Curtis, Gilbert, AZ (US)

(73) Assignee: MICROCHIP TECHNOLOGY INCORPORATED, Chandler, AZ (US)

( * ) Notice: Subject to any disclaimer, the term of this patent is extended or adjusted under 35 U.S.C. 154(b) by 420 days.

(21) Appl. No.: 13/667,269

(22) Filed: Nov. 2, 2012

(65) Prior Publication Data

US 2013/0154670 A1 Jun. 20, 2013

Related U.S. Application Data

(63) Continuation-in-part of application No. 13/633,686, filed on Oct. 2, 2012.

(60) Provisional application No. 61/570,418, filed on Dec. 14, 2011.

(51) Int. Cl.
| | |
|---|---|
| *G01N 27/70* | (2006.01) |
| *G01N 27/66* | (2006.01) |
| *G08B 17/10* | (2006.01) |
| *G08B 17/11* | (2006.01) |
| *G01R 27/26* | (2006.01) |

(52) U.S. Cl.
CPC ............... *G08B 17/11* (2013.01); *G01N 27/66* (2013.01); *G01R 27/2605* (2013.01)

(58) Field of Classification Search
USPC .......................................................... 324/469
See application file for complete search history.

(56) References Cited

U.S. PATENT DOCUMENTS

| | | | | |
|---|---|---|---|---|
| 3,295,121 A | * | 12/1966 | Meyer | 340/629 |
| 3,832,678 A | | 8/1974 | Gysell et al. | 340/587 |
| 4,213,047 A | * | 7/1980 | McCord | 250/381 |

(Continued)

FOREIGN PATENT DOCUMENTS

| | | | | |
|---|---|---|---|---|
| DE | 102009030495 A1 | 1/2011 | | G01B 7/00 |
| EP | 1719947 A1 | 11/2006 | | F23N 5/12 |

(Continued)

OTHER PUBLICATIONS

Yair, R., "Charge Sampling Method for Low Current Measurement," Review of Scientific Instruments, vol. 45, No. 3, 6 pages, Mar. 1974.

(Continued)

*Primary Examiner* — Melissa Koval
*Assistant Examiner* — Courtney McDonnough
(74) *Attorney, Agent, or Firm* — Slayden Grubert Beard PLLC

(57) ABSTRACT

A smoke detection sensor ion chamber has a capacitance and a change in the permittivity of that capacitance dielectric (ionized air in the chamber) may be used to detect the presence of smoke therein. Smoke from typical fires is mainly composed of unburned carbon that has diffused in the surrounding air and rises with the heat of the fire. The permittivity of the carbon particles is about 10 to 15 times the permittivity of clean air. The addition of the carbon particles into the air in the ion chamber changes in the permittivity thereof that is large enough to measure by measuring a change in capacitance of the ion chamber.

19 Claims, 6 Drawing Sheets

(56) References Cited

U.S. PATENT DOCUMENTS

| | | | |
|---|---|---|---|
| 4,222,045 A * | 9/1980 | Cholin | 340/628 |
| 4,260,984 A | 4/1981 | Honma | 340/630 |
| 4,266,220 A * | 5/1981 | Malinowski | 340/628 |
| 4,401,978 A | 8/1983 | Solomon | 340/628 |
| 4,538,137 A | 8/1985 | Kimura | 340/512 |
| 4,652,866 A | 3/1987 | Siegmann et al. | 340/628 |
| 5,173,683 A | 12/1992 | Brighenti et al. | 340/505 |
| 5,243,330 A | 9/1993 | Thuillard | 340/629 |
| 5,422,807 A | 6/1995 | Mitra et al. | 700/79 |
| 5,633,591 A | 5/1997 | Childress et al. | 324/399 |
| 5,705,988 A | 1/1998 | McMaster | 340/628 |
| 5,966,078 A | 10/1999 | Tanguay | 340/636.1 |
| 6,257,049 B1 | 7/2001 | Greybush | 73/29.01 |
| 6,433,712 B1 | 8/2002 | Ohnhaeuser et al. | 341/118 |
| 6,661,346 B1 | 12/2003 | Wood et al. | 340/601 |
| 6,981,090 B1 | 12/2005 | Kutz et al. | 710/317 |
| 7,288,946 B2 | 10/2007 | Hargreaves et al. | 324/678 |
| 7,307,485 B1 * | 12/2007 | Snyder et al. | 331/150 |
| 7,382,140 B2 | 6/2008 | Obrecht | 324/678 |
| 7,460,441 B2 | 12/2008 | Bartling | 368/118 |
| 7,764,213 B2 | 7/2010 | Bartling et al. | 341/152 |
| 8,031,094 B2 | 10/2011 | Hotelling et al. | 341/143 |
| 8,487,655 B1 | 7/2013 | Kutz et al. | 326/86 |
| 8,547,135 B1 | 10/2013 | Yarlagadda et al. | 326/38 |
| 8,847,802 B2 | 9/2014 | Lundstrum et al. | 341/141 |
| 8,884,771 B2 | 11/2014 | Cooke et al. | 340/628 |
| 8,981,754 B1 | 3/2015 | Rohilla et al. | 323/312 |
| 2002/0078744 A1 | 6/2002 | Gehman et al. | 73/204.11 |
| 2002/0101345 A1 | 8/2002 | Pattok et al. | 340/516 |
| 2002/0153923 A1 | 10/2002 | Piasecki et al. | 326/57 |
| 2003/0058114 A1 | 3/2003 | Miller | 340/577 |
| 2004/0257235 A1 | 12/2004 | Right et al. | 340/628 |
| 2005/0030172 A1 * | 2/2005 | Right et al. | 340/521 |
| 2007/0075710 A1 | 4/2007 | Hargreaves et al. | 324/658 |
| 2008/0012715 A1 | 1/2008 | Montgomery | 340/579 |
| 2008/0079148 A1 | 4/2008 | Leung et al. | 257/734 |
| 2008/0111714 A1 | 5/2008 | Kremin | 341/33 |
| 2008/0272826 A1 | 11/2008 | Smit et al. | 327/509 |
| 2008/0312857 A1 | 12/2008 | Sequine | 702/65 |
| 2009/0230305 A1 | 9/2009 | Burke et al. | 250/336.1 |
| 2009/0256817 A1 | 10/2009 | Perlin et al. | 345/174 |
| 2010/0059295 A1 | 3/2010 | Hotelling et al. | 178/18.06 |
| 2010/0060593 A1 | 3/2010 | Krah | 345/173 |
| 2010/0097015 A1 | 4/2010 | Knoedgen et al. | 318/135 |
| 2010/0102832 A1 | 4/2010 | Bartling et al. | 324/679 |
| 2010/0181180 A1 | 7/2010 | Peter | 200/5 R |
| 2010/0231241 A1 | 9/2010 | Mueck et al. | 324/686 |
| 2010/0283760 A1 | 11/2010 | Leung et al. | 345/174 |
| 2010/0287571 A1 | 11/2010 | Mohammed et al. | 719/328 |
| 2010/0295555 A1 * | 11/2010 | Emanuel et al. | 324/601 |
| 2011/0007028 A1 | 1/2011 | Curtis et al. | 345/174 |
| 2011/0234417 A1 | 9/2011 | Aleman et al. | 340/660 |
| 2011/0267287 A1 | 11/2011 | Bartling et al. | 345/173 |
| 2011/0267309 A1 | 11/2011 | Hanauer et al. | 345/174 |
| 2012/0005693 A1 | 1/2012 | Mohammed et al. | 719/328 |
| 2012/0098686 A1 | 4/2012 | Wang | 341/118 |
| 2012/0112728 A1 | 5/2012 | Bodo et al. | 323/311 |
| 2013/0088246 A1 | 4/2013 | Lundstrum et al. | 324/686 |
| 2013/0090873 A1 | 4/2013 | Lundstrum et al. | 702/64 |
| 2013/0126715 A1 | 5/2013 | Flaherty | 250/214 R |
| 2013/0298100 A1 | 11/2013 | Hastings et al. | 716/126 |
| 2013/0322439 A1 | 12/2013 | Verhollen et al. | 370/389 |

FOREIGN PATENT DOCUMENTS

| | | | | |
|---|---|---|---|---|
| FR | 2473201 A1 | | 7/1981 | G08B 17/11 |
| GB | 1313877 A | * | 11/1970 | G01N 21/27 |
| GB | 1598821 A | | 9/1981 | G08B 17/11 |
| GB | 2117560 A | | 10/1983 | G01N 27/64 |
| GB | 2156126 A | | 10/1985 | G08B 17/00 |
| WO | 2006/138205 A1 | | 12/2006 | H03M 1/06 |

OTHER PUBLICATIONS

Margarita, Andrey, "Application Note AN2245: Smart Smoke Detector," Cypress Semiconductor Corporation, XP055054690, URL: http://www.psocdeveloper.com/uploads/tx_piapappnote/an2245_01.pdf, 12 pages, Feb. 22, 2005.

Perme, Thomas, "AN1101: Introduction to Capacitive Sensing," Microchip Technology, Inc., XP002693941, URL: http://ww1.microchip.com/downloads/en/AppNotes/01101A.pdf, 10 pages, Jun. 25, 2007.

Bohn, Bruce, "AN1250: Microchip CTMU for Capacitive Touch Applications," Microchip Technology, Inc., XP055007432, URL: http://www.microchip.com/stellent/idcplg?IdcService=SS_GET_PAGE&nodeID=1824&appnote=en539441, 22 pages, Feb. 3, 2009.

Perme, Thomas et al., AN1298: Capacitive Touch Using Only an ADC ("CVD"), Microchip Technology, Inc., XP055007357, URL: http://www.microchip.com/stellent/idcplg?IdcService=SS_GET_PAGE&nodeId=1824&appnote=en545264, 4 pages, Oct. 7, 2009.

Davison, Burke, "AN1334: Techniques for Robust Touch Sensing Design," Microchip Technology, Inc., XP055047201, URL: http://www.microchip.com/downloads/en/AppNotes/01334A.pdf, 28 pages, Aug. 6, 2010.

Yedamale, Padmaraja et al., "AN1375: See What You Can Do with the CTMU," Microchip Technology, Inc., XP055047211, URL: http://www.microchip.com/downloads/en/AppNotes/CTMU%2001375a.pdf, 12 pages, May 11, 2011.

Anonymous, "Delta-Sigma Modulation," Wikipedia, URL: http://en.wikipedia.org/w/index.php?title=Special:Book&bookcmd=download&collection_id=fa136df1282a073a&writer=r1&return_to=Delta-sigma modulation, 14 pages, 2012.

International Search Report and Written Opinion, Application No. PCT/US2012/058682, 12 pages, Dec. 17, 2012.

International Search Report and Written Opinion, Application No. PCT/US2012/058691, 13 pages, Dec. 19, 2012.

International Search Report and Written Opinion, Application No. PCT/US2012/058832, 11 pages, Jan. 22, 2013.

International Search Report and Written Opinion, Application No. PCT/US2012/058837, 14 pages, Feb. 18, 2013.

International Search Report and Written Opinion, Application No. PCT/US2012/058716, 10 pages, Mar. 15, 2013.

International Search Report and Written Opinion, Application No. PCT/US2012/069086, 10 pages, Apr. 5, 2013.

International Search Report and Written Opinion, Application No. PCT/US2012/069094, 12 pages, Apr. 5, 2013.

International Search Report and Written Opinion, Application No. PCT/US2012/058688, 11 pages, Apr. 5, 2013.

International Search Report and Written Opinion, Application No. PCT/US2012/069076, 11 pages, Apr. 10, 2013.

International Search Report and Written Opinion, Application No. PCT/US2012/070466, 13 pages, Apr. 24, 2013.

International Search Report and Written Opinion, Application No. PCT/US2013/052956, 12 pages, Jan. 28, 2014.

U.S. Appl. No. 13/709,399, 3 pages, Sep. 8, 2015.

* cited by examiner

METHOD AND APPARATUS FOR DETECTING SMOKE IN AN ION CHAMBER

RELATED PATENT APPLICATION

This application claims priority to commonly owned U.S. Provisional Patent Application Ser. No. 61/570,418; filed Dec. 14, 2011; entitled "Method and Apparatus for Detecting Smoke," by Benjamin T. Cooke, Joseph Julicher and Keith Edwin Curtis; and is a Continuation-In-Part of U.S. patent application Ser. No. 13/633,686; filed Oct. 2, 2012; entitled "Differential Current Measurements to Determine Ion Current in the Presence of Leakage Current," by Joseph Julicher, Keith Curtis and Paul N. Katz; both of which are hereby incorporated by reference herein for all purposes.

TECHNICAL FIELD

The present disclosure relates to smoke detection devices, and more particularly, to a smoke detection device that uses a change in permittivity that affects a capacitance value of an ion chamber when smoke is introduced therein.

BACKGROUND

A smoke detector generally uses an ionization chamber containing a radioactive ion source that is coupled to a high input impedance operational amplifier. FIG. 1 shows a typical ionization chamber used in a smoke detector to produce a very small current (nA) that is reduced in the presence of smoke particles. Operational amplifiers are used to convert this current to a voltage that is then measured to determine the presence of smoke. Elevated temperatures cause increased leakage currents on the inputs of the operational amplifier in the smoke detector. This affects overall performance of the ionization chamber smoke detection function. Thus, such increases in leakage currents can pose a variety of problems such as inaccuracy, etc. which may require further compensation circuits when designing a smoke detector and therefore may increase the cost of the device.

Furthermore, the impedance of the ion chamber is extremely high, and any leakage currents, e.g., printed circuit board leakage current, masks the ion chamber current. Smoke detection ion chambers therefore require a complex manufacturing process where pins of the sensing integrated circuit operational amplifier are bent and directly welded in mid-air to the ion chamber. As mentioned above, special low leakage circuits are required to detect the small current change through the ion chamber caused by the presence of smoke therein.

SUMMARY

Therefore, a need exists for a way to detect smoke in an ion chamber of a smoke detector that does not require sensitive and expensive components nor complex manufacturing processes.

According to an embodiment, a method for detecting smoke may comprise the steps of: coupling an ionization chamber to a capacitive sensing module (CSM); determining a change in a capacitance of the ionization chamber using the CSM; and detecting the presence of smoke by detecting a predetermined change in the capacitance.

According to a further embodiment of the method, the step of determining the change in the capacitance of the ionization chamber further may comprise the steps of: determining a first change in the capacitance of the ionization chamber when the ionization chamber may be at a first polarity; determining a second change in the capacitance of the ionization chamber when the ionization chamber may be at a second polarity; determining a difference between the first change and the second change; and using the difference in determining the change in the capacitance of the ionization chamber. According to a further embodiment of the method, the predetermined change in the capacitance may be a change in the capacitance within a certain time.

According to a further embodiment of the method, the step of determining the change in the capacitance of the ionization chamber may comprise the steps of: charging the capacitance of the ionization chamber with a first constant current source until a charge on the capacitance may be at a first voltage, then discharging the capacitance of the ionization chamber with a second constant current source until the charge on the capacitance of the ionization chamber may be at a second voltage, and then repeating charging the capacitance; counting the number of times the charge on the capacitance of the ionization chamber may be at the first or the second voltage within a certain time period; and comparing the count numbers of subsequent time periods to determine whether the count number of any one or more of the subsequent time periods has changed by a certain number of counts.

According to a further embodiment of the method, the step of determining the change in the capacitance of the ionization chamber may comprise the steps of: charging the capacitance of a first ionization chamber open to smoke entrance with a first constant current source until a charge on the capacitance of the first ionization chamber may be at a first voltage, then discharging the capacitance of the first ionization chamber with a second constant current source until the charge on the capacitance of the first ionization chamber may be at a second voltage, and then repeating charging the capacitance of the first ionization chamber; counting the number of times the charge on the capacitance of the first ionization chamber may be at the first or the second voltage within a certain time period; charging the capacitance of a second ionization chamber closed to smoke entrance with the first constant current source until a charge on the capacitance of the second ionization chamber may be at a first voltage, then discharging the capacitance of the second ionization chamber with the second constant current source until the charge on the capacitance of the second ionization chamber may be at the second voltage, and then repeating charging the capacitance of the second ionization chamber; counting the number of times the charge on the capacitance of the second ionization chamber may be at the first or the second voltage within a certain time period; and subtracting a count number of the first ionization chamber from a count number of the second ionization chamber and dividing by the count number of the second ionization chamber.

According to a further embodiment of the method, in a first measurement, a housing of the ionization chamber may be coupled to the CSM; and in a second measurement, a collector plate of the ionization chamber may be coupled to the CSM.

According to a further embodiment of the method, further steps may comprise the steps of subtracting a measurement value of the first measurement from a measurement value of the second measurement then dividing by the second measurement value; and comparing the count numbers of subsequent time periods to determine whether the count number of any one or more of the subsequent time periods has changed by a certain number of counts. According to a further embodiment of the method, further steps may comprise the step of compensating for temperature change with temperature information from a temperature sensor. According to a further embodiment of the method, further steps may comprise the step of compensating for relative humidity change with relative humidity information from a relative humidity sensor. According to a further embodiment of the method, a further step may comprise the step of compensating for voltage change with voltage information from a voltage sensor.

According to another embodiment, an apparatus for detecting smoke may comprise: an ionization chamber coupled to a capacitive sensing module (CSM) for determining a capacitance of the ionization chamber; wherein a predetermined change in the capacitance of the ionization chamber indicates the presence of smoke in the ionization chamber.

According to a further embodiment, circuits may be provided for alternately coupling to the ionization chamber at a first polarity for determining a first capacitance of the ionization chamber and coupling to the ionization chamber at a second polarity for determining a second capacitance of the ionization chamber, whereby a difference between the first and second capacitances may be used in determining the presence of smoke in the ionization chamber.

According to a further embodiment, the CSM may be a peripheral device in a microcontroller. According to a further embodiment, a digital processor and memory may be coupled to the CSM and an alarm circuit. According to a further embodiment, a temperature sensor may be coupled to the digital processor and a temperature compensation look-up table stored in the memory coupled to the digital processor and used to compensate temperature induced changes of the capacitance of the ionization chamber. According to a further embodiment, a humidity sensor may be coupled to the digital processor and a humidity compensation look-up table stored in the memory coupled to the digital processor and used to compensate humidity induced changes of the capacitance of the ionization chamber.

According to a further embodiment, a voltage sensor may be coupled to the digital processor and a voltage compensation look-up table stored in the memory coupled to the digital processor and used to compensate voltage induced changes of the capacitance of the ionization chamber. According to a further embodiment, an audible alert may be actuated by the presence of smoke in the ionization chamber. According to a further embodiment, a visual alert may be actuated by the presence of smoke in the ionization chamber.

According to still another embodiment, an apparatus for detecting smoke may comprise: a first ionization chamber coupled to a capacitive sensing module (CSM) for determining a capacitance of the first ionization chamber, wherein the first ionization chamber may be open to smoke entrance; a second ionization chamber coupled to the CSM for determining a capacitance of the second ionization chamber, wherein the second ionization chamber may be closed to smoke entrance; wherein a predetermined difference in the capacitances of the first and second ionization chambers indicates the presence of smoke in the first ionization chamber.

BRIEF DESCRIPTION OF THE DRAWINGS

A more complete understanding of the present disclosure may be acquired by referring to the following description taken in conjunction with the accompanying drawings wherein.

Figure 1:
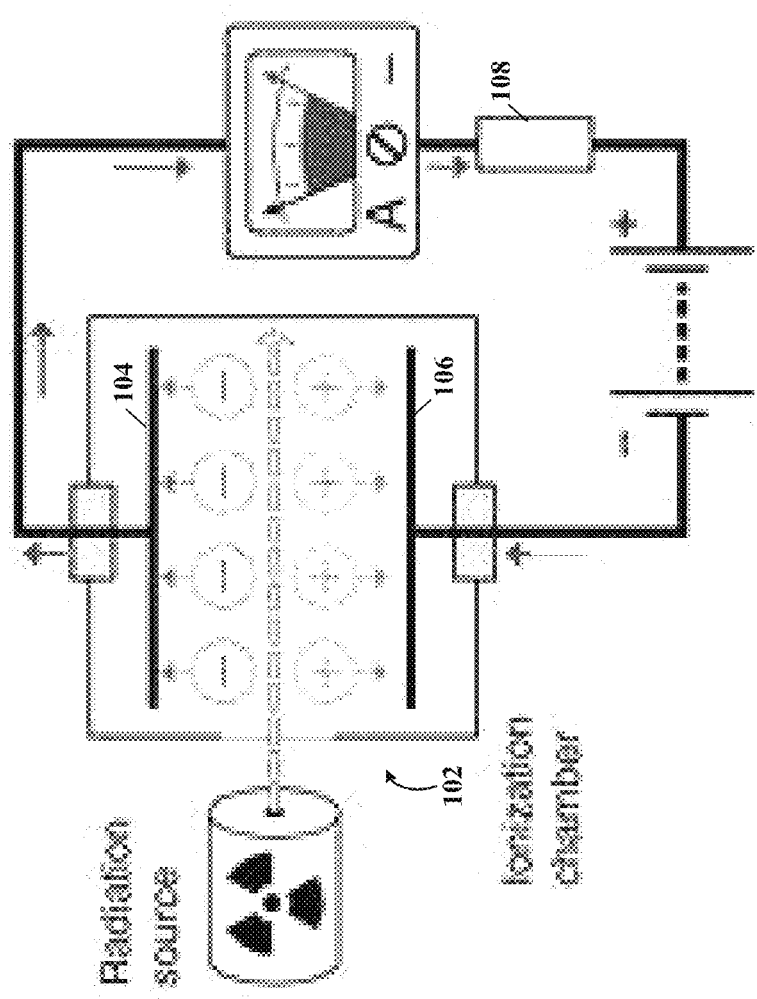
FIG. 1 illustrates a schematic diagram of an ion chamber having a radiation source and used as a smoke detection sensor.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

A radioactive source in an ion chamber causes some of the gas (e.g., air) in the chamber to ionize. The results is a higher than normal permittivity of the gas due to the higher than normal number of electrically polarized (ionized) gas molecules. When smoke enters the ion chamber, the smoke reacts with the ionized gas molecules thereby changing the permittivity, $\in$, thereof. The ion chamber may be characterized as a leaky capacitor with the amount of leakage current determined by the ion flow between charged plates 102 and 104 (FIG. 1) of the ion chamber. A capacitance, C, of a capacitor formed by plates 102 and 104 is a function of the area, A, of the conductive plates 102 and 104; the distance, d, between the plates 102 and 104; and the permittivity, $\in$, of the dielectric (air) therebetween according to the formula: $C=\in A/d$. Thus a change in the permittivity of the gas in the ion chamber also changes the capacitance value thereof. Therefore, by using a capacitance measuring function, e.g., a capacitive sensing module (CSM) in a microcontroller, the capacitance value change caused by the permittivity change of the gas dielectric of this leaky capacitor can be detected to determine the presence of smoke therein.

Capacitive sensing using the period method and a capacitive sensing module (CSM), according to the teachings of this disclosure, are more fully described in Application Notes AN1101, AN1171, AN1268, AN1312, AN1334 and TB3064, available at www.microchip.com, and commonly owned U.S. Patent Application No.: US 2011/0007028 A1, entitled "Capacitive Touch System With Noise Immunity" by Keith E. Curtis, et al.; wherein all of which are hereby incorporated by reference herein for all purposes. It is also contemplated and within the scope of this disclosure that any type of capacitance measurement circuit having the necessary resolution may be used in determining the capacitance value and/or change in the capacitance value of the ion chamber, and that a person having ordinary skill in the art of electronics and having the benefit of this disclosure could implement such a capacitance measurement circuit.

Temperature and battery voltage variations can make significant differences in the permittivity of the gas (air) with corresponding variations in the capacitance measurements of a first ion chamber. By providing a second ion chamber that is sealed from smoke entering, a comparison of the measured capacitance values of each of the first and second ion chambers can be used to compensate for these variations and provide a sensitive way of detecting smoke particles. For example, subtracting the first ion chamber capacitance value from the second ion chamber capacitance value and then dividing by the second ion chamber capacitance value, removes the temperature and battery voltage effects, leaving a resultant value with is primarily affected by the presence of smoke in the first ion chamber.

Temperature, relative humidity (RH) and/or battery voltage sensors may be incorporated into a smoke detection system for determining the compensation necessary for the capacitance measurements of the ion chamber used for smoke detection. Permittivity variations due to temperature, RH and/or voltage changes generally are over a longer time period than a sudden change in the amount of contaminates (carbon particles, etc.) in the air between the plates of the ion chamber capacitor. Another less sensitive way to ignore permittivity variations due to temperature, RH and/or voltage changes, would be to use an envelope detection or averaging process to ignore the slow drift of ion chamber capacitance due to voltage and/or temperature changes but recognize a more abrupt (rapid) change of the permittivity of air due to carbon particles suddenly showing up in the ion chamber. Various techniques for measuring changes in capacitance may be used and are contemplated herein for all purposes. Those having ordinary skill in capacitor measurement circuits and the benefit of this disclosure could readily apply those capacitor measurement circuits in a smoke detection apparatus. A mixed signal (analog and digital functions) microcontroller may used for capacitance measurements, e.g., CSM, doing the calculations necessary to determine whether smoke is present in the ion chamber, and compensate for and/or average out permittivity changes due to temperature, RH and/or battery voltage changes.

Referring now to the drawing, the details of specific example embodiments are schematically illustrated. Like elements in the drawings will be represented by like numbers, and similar elements will be represented by like numbers with a different lower case letter suffix.

Referring to FIG. 1, depicted is a schematic diagram of an ion chamber having a radiation source and used as a smoke detection sensor. The ion chamber 102 may be characterized as a capacitor with some ionized gas molecules between the capacitor plates 104 and 106. The gas molecules are ionized by the radiation source and when a voltage is applied between the two capacitor plates 104 and 106 a current will flow through the ionized gas and a resistor 108 connected in series with the capacitor plates 104 and 106. This current produces a voltage across the resistor 108. By measuring the voltage across the resistor 108, the permittivity, $\in$, of the gas may be determined. Smoke in the ion chamber will cause an abrupt change in the permittivity, $\in$, causing an abrupt change in the current flow and voltage across the resistor 108. This voltage is measured by a very high impedance operational amplifier (not shown) which requires complex circuitry and manufacturing processes. A better way, according to the teachings of this disclosure, is to measure the capacitance values of the ion chamber before and after smoke entry therein. As the ionized gas permittivity, $\in$, changes so does the capacitance value of the ion chamber. By using a capacitive measurement module having high enough capacitance value measurement resolution, the change in capacitance caused by smoke entry into the ion chamber may be detected and used to generate a smoke detection alarm.

Figure 1A:
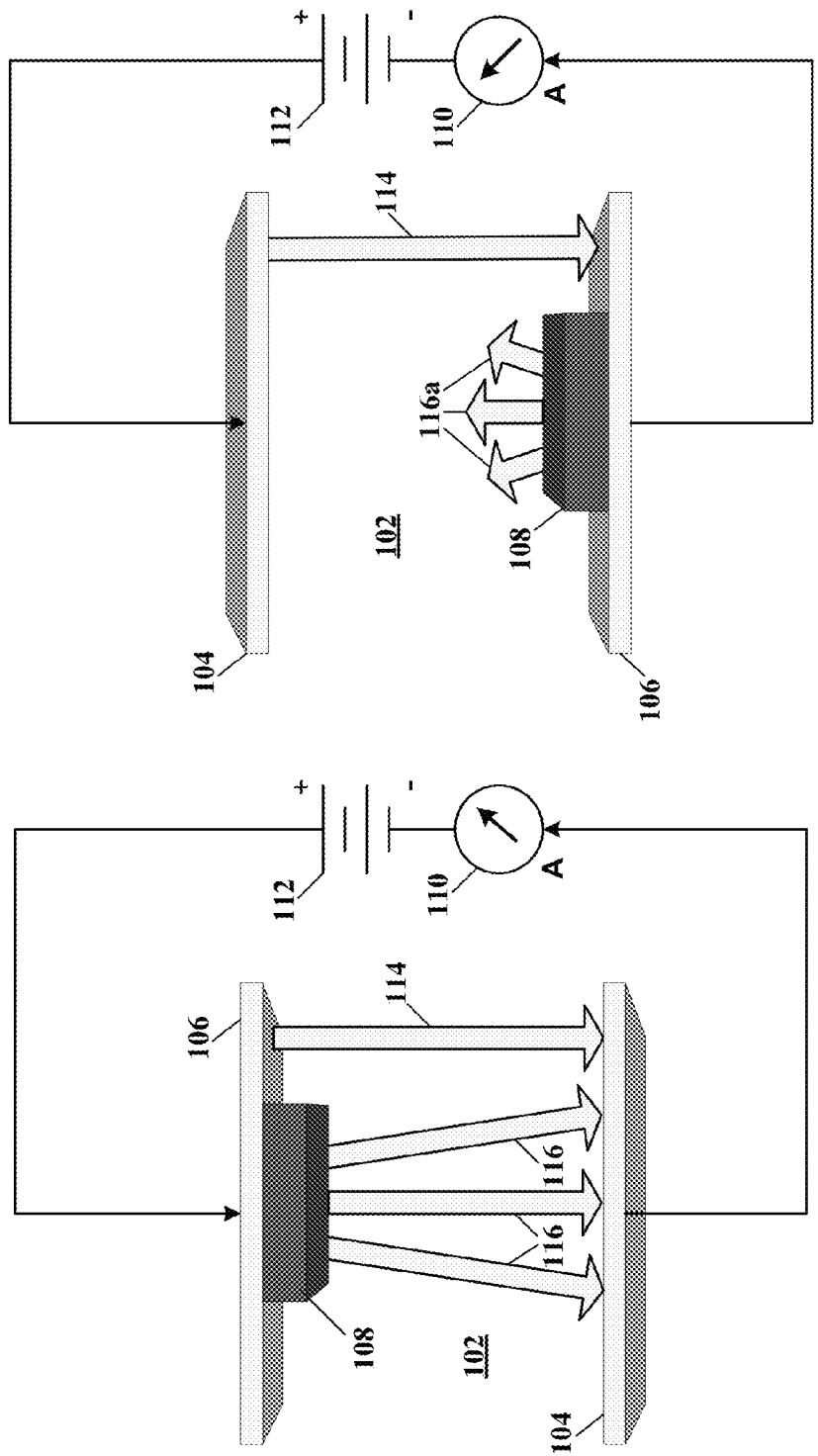
FIG. 1A illustrates schematic diagrams of an ion chamber having a radiation source and showing current flows therethrough for different polarity voltage source connections thereto.

Referring to FIG. 1A, depicted are schematic diagrams of an ion chamber having a radiation source and showing current flows therethrough for different polarity voltage source connections thereto. The ion chamber 102 may be characterized as three electrodes, e.g., electrodes 104, 106 and 210, having some ionized gas (e.g., air) molecules therebetween. The gas molecules are ionized by a radiation source 108. When a voltage potential 112 is applied between the two electrodes 104 and 106 at a first polarity (positive to electrode 106 and negative to electrode 104), a positively biased ionization electron current 116, $I_{chamber}$, will flow through the ionized gas. When the voltage potential 112 is applied between the two electrodes 104 and 106 at a second polarity (positive to electrode 104 and negative to electrode 106), substantially no negatively biased ionization electron current 116a will flow through the ionized gas since now the electrode 104 will repel the ionized gas electrons. However, leakage current 114, $I_{leakage}$, e.g., printed circuit board contaminates, grease, dust, etc., will flow irrespective of the connected polarity of the voltage potential 112.

Thus when the voltage potential 112 is connected at the first polarity across chamber 102 electrodes 104 and 106, the total current flow through the current meter 110 is the ionized electron current 116, $I_{chamber}$, plus the leakage current 114, $I_{leakage}$. And when the voltage potential 112 is connected at the second polarity across chamber 102 electrodes 104 and 106, the total current flow through the current meter 110 is substantially no ionized electron current 116a plus the leakage current 114, $I_{leakage}$, which results in substantially only the leakage current 114, $I_{leakage}$. Therefore, by subtracting the leakage current 114, $I_{leakage}$, from the total current flow, the actual ionized electron current 116, $I_{chamber}$, may be determined. This allows more sensitive measurements of any change in the ionized electron current 116, $I_{chamber}$, without these changes being masked by the undesired leakage current 114, $I_{leakage}$. It is contemplated and within the scope of this disclosure that any fluid, e.g., gas or liquid, that can be ionized by the ion source 108 will function as described hereinabove.

Figure 2:
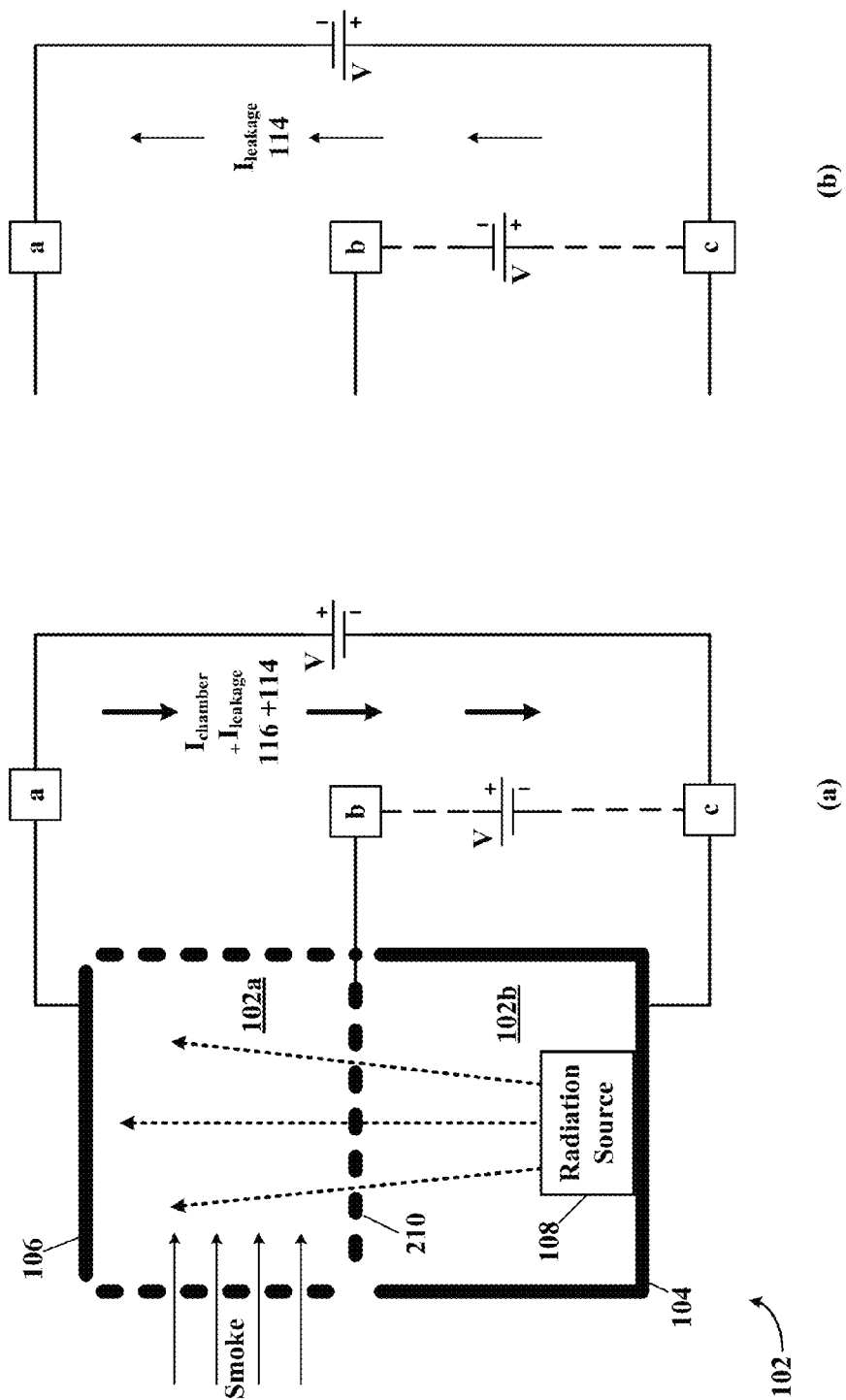
FIG. 2 illustrates a schematic elevational view of a typical ion chamber used as a smoke detection sensor.

Referring to FIG. 2, depicted is a schematic elevational view of a typical two chamber smoke detection sensor having a radiation source. The ion chamber 102 is comprised of two chambers 102a and 102b. The top chamber 102a is open to ingress of smoke therein, and the bottom chamber 102b is closed to smoke ingress. A conductive screen 210 is located between the two chambers 102a and 102b. The radiation source 108 proximate to or in the ion chamber 102 causes some of the gas in the chambers 102a and 102b to ionize. This ionization of the gas within the chambers 102a and 102b causes an ionization current 116, $I_{chamber}$, through both chambers 102a and 102b to increase between the electrodes 104 and 106 of the ion chamber 102.

When smoke is present in the top chamber 102a, it combines with the ionized gas, neutralizing some of the ionized gas from the current path of the ionization current 116, $I_{chamber}$. As a result the permittivity of the top chamber 102a is smaller than it is in the lower chamber 102b. The ionization current 116, $I_{chamber}$, flows in series through chambers 102a and 102b and therefore will be lower when smoke is in the chamber 102a. When the voltage across the chambers 102a and 102b is reversed substantially no reverse ionization current 116a will flow and the only current flow between the electrodes 104 and 106 will be the leakage current 114. The presence of the leakage current 114 reduces the sensitivity in measuring changes in the ionization current 116. By removing this common mode leakage current 114 from the determination of smoke in the chamber 102a, a more sensitive smoke detector results.

Figure 3:
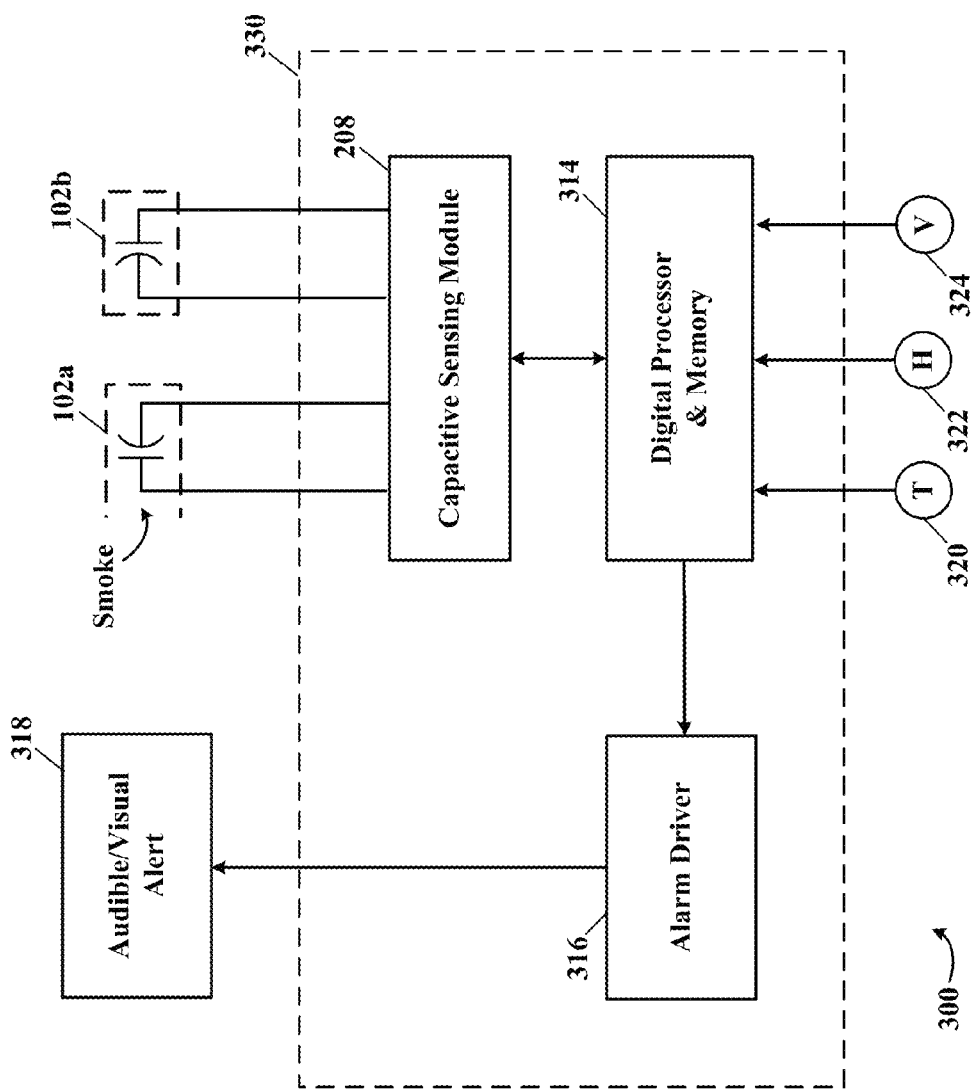
FIG. 3 illustrates a schematic block diagram of a smoke detector, according to a specific example embodiment of this disclosure.

Referring to FIG. 3, depicted is a schematic block diagram of a smoke detector, according to a specific example embodiment of this disclosure. A smoke detector, generally represented by the numeral 300, may comprise a capacitive sensing module 208, a smoke detection sensor ion chamber 102a, a digital processor and memory 314, an alarm driver 316, and an audible/visual alert 318. The capacitive sensing module 208, digital processor and memory 314, and alarm driver 316 may be provided in an integrated circuit microcontroller 330. The smoke detection sensor ion chamber 102a is coupled to the capacitive sensing module 208 wherein representations of capacitance values thereof are measured and then each representative capacitance value is read by and processed in the digital processor and memory 314. When there is a change in the capacitance value representations within a certain time, the digital processor 314 will enable the alarm driver 316 which turns on the audible/visual alert 318 to indicate the presence of smoke in the location of the smoke detector 300.

The smoke detector 300 may further comprise a second ion chamber 102b that is closed to outside air that may contain smoke. The first and second ion chambers 102a and 102b may be used for making a comparison of the measured capacitance values of each of the first and second ion chambers 102a and 102b, and compensate for these variations, thereby providing for a more sensitive way of detecting smoke particles, as more fully described hereinabove.

The smoke detector 300 may further comprise a temperature sensor 320, a relative humidity sensor 322, and/or a voltage sensor 324 coupled to a power supply, e.g., battery (not shown). Wherein the digital processor 314 may compensate for capacitance measurements that may change under different temperature, humidity and/or voltage conditions, e.g., using look-up tables that contain calibration and compensation data for the smoke sensor ion chamber 102. In addition, the digital processor 314 may perform smoothing, time averaging, noise suppression, over sampling, and/or digital signal processing to enhance the capacitance change detection sensitivity and/or reduce noise pick-up.

Figure 4:
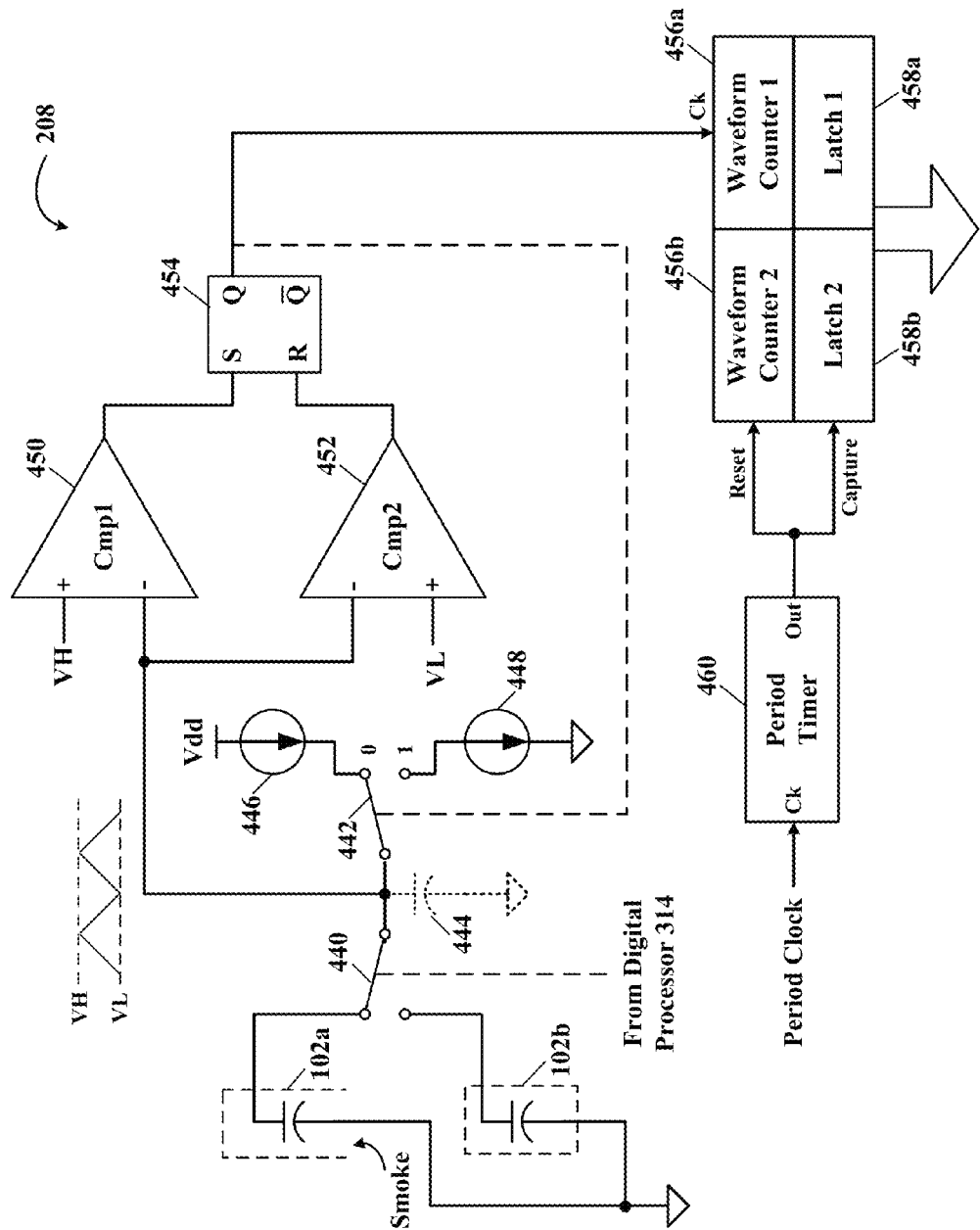
FIG. 4 illustrates a schematic block diagram of the capacitive sensing module shown in FIG. 3.

Referring to FIG. 4, depicted is a schematic block diagram of the capacitive sensing module shown in FIG. 3. The Capacitive Sensing Module (CSM) 208 measures capacitance based upon a relaxation oscillator methodology. The CSM 208 produces an oscillating voltage signal for measurement by a frequency determining circuit, at a frequency dependent upon the capacitance of the ion chamber 102. The frequency at which the CSM 208 generates the oscillating voltage signal will change when smoke is introduced into the ion chamber 102a. This change in frequency indicates smoke being present in the ion chamber 102a. Also a further enhancement to more reliable smoke detection is to require that the change in frequency occurs in less than or equal to a certain time period so as to reject slow frequency change due to changes in temperature, relative humidity and/or supply voltage (e.g., battery not shown).

The Capacitive Sensing Module (CSM) 208 may comprise an ion chamber selection switch 440, a current source selection switch 442, an internal or external capacitor 444, a first constant current source 446, a second constant current source 448, a first voltage comparator 450, a second voltage comparator 452, an RS flip-flop 454, waveform counter(s) 456, latch(es) 458, and a period timer 460. The selection switch 440 may be controlled by the digital processor 314 to select between ion chambers 102a and 102b. The capacitor 444 may be added in parallel with the capacitance of the ion chamber 102 for lowering the oscillation frequency. The current source selection switch 442 couples either the first constant current source 446 or the second constant current source 448 to the capacitance of the ion chamber 102 (and capacitor 444 if used). Comparators 450 and 452 monitor the charging/discharging voltage on the capacitance of the ion chamber 102 (and capacitor 444 if used).

An oscillating triangular voltage waveform is generated by the first constant current source 446 charging the capacitance of the ion chamber 102 (and capacitor 444 if used) and the second constant current source 448 discharging the capacitance of the ion chamber 102 (and capacitor 444 if used). The RS flip-flop 454 controls the current source selection switch 442 as follows: When the voltage on the capacitance of the ion chamber 102 (and capacitor 444 if used) (charging) reaches voltage VH, the output of the first voltage comparator 450 goes to a logic 1 and "sets" the Q-output of the RS flip-flop 454 to a logic 1, thereby causing the current source selection switch 442 to select the second constant current source 448, whereby the capacitance of the ion chamber 102 (and capacitor 444 if used) start to discharge through the second constant current source 448. When the voltage on the capacitance of the ion chamber 102 (and capacitor 444 if used) (discharging) reaches voltage VL, the output of the second voltage comparator 452 goes to a logic 1 and "resets" the Q-output of the RS flip-flop 454 to a logic 0, thereby causing the current source selection switch 442 to select the first constant current source 446, whereby the capacitance of the ion chamber 102 (and capacitor 444 if used) start to charge through the first constant current source 446. Switches 440 and 442 may be solid state field effect transistor (FET) switches.

This switching oscillation between the two charging and discharging constant current sources 450 and 452, respectively, have an oscillation frequency dependent upon the capacitance value of the ion chamber 102 (and capacitor 444 if used). If the ion chamber 102 capacitance value increases then the oscillation frequency decreases and if the capacitance value decreases then the oscillation frequency increases. By accurately measuring this oscillation frequency, detection of a capacitance change (e.g., smoke) may be determined.

A waveform counter 456 may be used to count the number of cycles of the oscillation waveform (e.g., positive going logic levels from Q output of the RS flip-flop 454) within a certain time period. If the time period of counting and number of cycles within the time period are known, the frequency of the waveform may be determined. However since only a change in the capacitance value is of interest, just comparing the number of cycles within different time periods is all that is necessary in determining whether there is smoke in the ion chamber 102a. Waveform counters 456a and 456b may be concatenated and/or a high resolution counter (timer) may be, for example but not limited to, 24 or 32 bits. A high resolution period timer 460 provides accurate time periods for determining the number of cycles of the oscillation waveform in each of the time periods. Latch(es) 458 capture the number of cycles counted in the waveform counter(s) 456 for each time period and the digital processor may then read the cycle count per time period of the oscillation waveform from the latch(es) 458.

According to various embodiments, in one measurement the housing 106 of the ion chamber 102a (FIG. 2) may be coupled in parallel with the internal capacitor 444 and the respective resulting frequency may be measured. In another measurement the internal collector plate 104 of the ion chamber 102a may be connected in parallel with the internal capacitor 444. Subtracting the ion chamber 102a capacitance value from the ion chamber 102b capacitance value and dividing by the ion chamber 102b capacitance value, removes temperature and battery voltage effects, leaving a capacitance value which is primarily affected by the presence of smoke in the ion chamber 102a.

Figure 5:
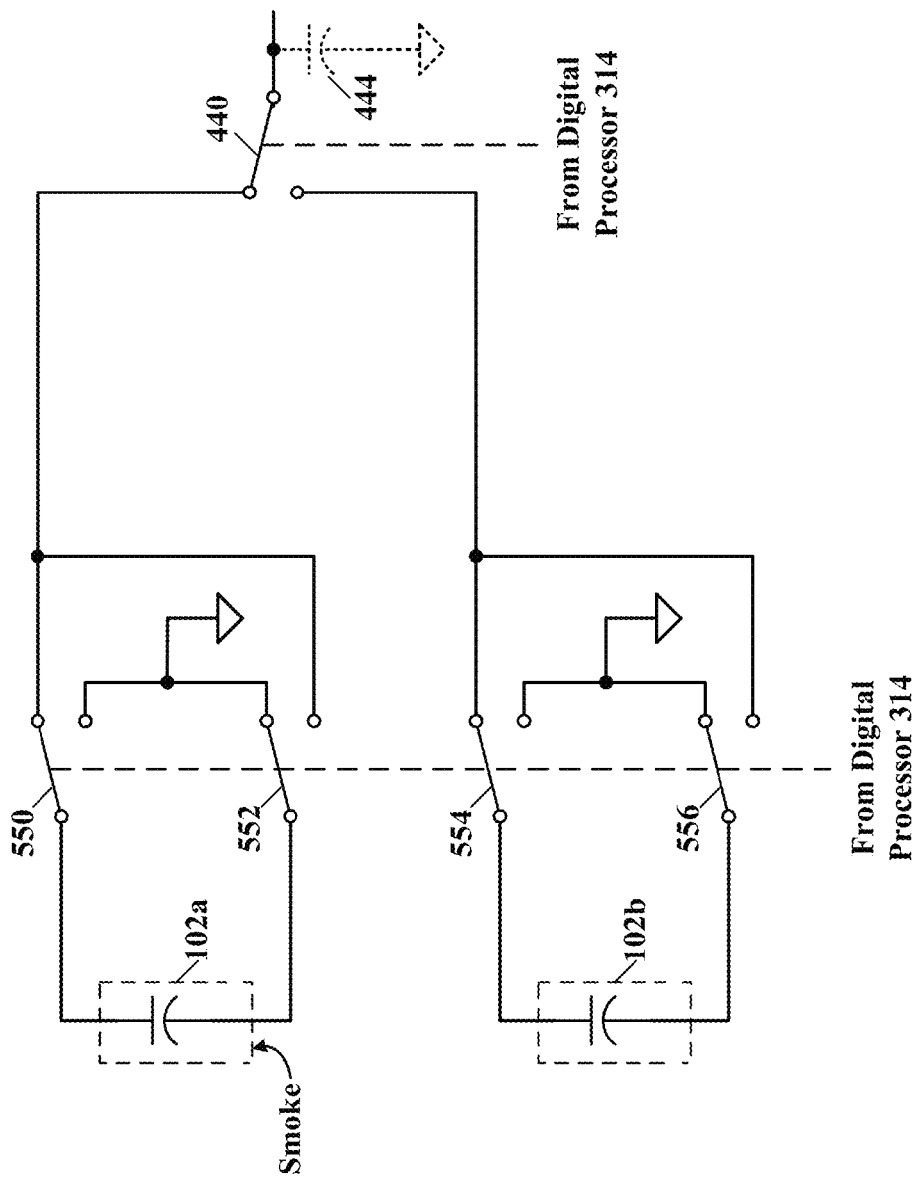
FIG. 5 illustrates a schematic block diagram of a portion of the capacitive sensing module shown in FIG. 3 showing switching means used in rejecting common mode leakage current, according to another specific example embodiment of this disclosure.

Referring to FIG. 5, depicted is a schematic block diagram of a portion of the capacitive sensing module shown in FIG. 3 showing switching means used in rejecting common mode leakage current, according to another specific example embodiment of this disclosure. Switches 550 and 552, and 554 and 556 change the polarity connections of the chambers 102a and 102b, respectively. Two sample counts of each of the chambers 102a and 102b are taken, one sample count at a first polarity and a second sample count at a second polarity opposite the first polarity. These sample count values are stored in the memory of the digital processor 314 for further computational processing, e.g., subtracting the lower sample count value from the higher sample count value of each chamber 102a and 102b, thereby canceling out what is caused by the leakage current 114, with a result of only a representation of the chamber ionization current 116. Since each chamber 102a and 102b is independently measured, any difference in the ionization currents 116 of the two chambers will indicate influence of smoke on the ionization of the gas in the chamber 102a. Determining a count value representing the ionization current 116 of the closed to the count value representing the smoke ionization chamber 102b thereby allows a base value that can be used to track or "float" a base count reference value for chamber 102a so that a small change thereof can be more easily recognized as indicating detection of smoke therein.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A method for detecting smoke, comprising the steps of:
coupling an ionization chamber to a capacitive sensing module (CSM);
determining a change in a capacitance of the ionization chamber using the CSM by:
determining a first change in the capacitance of the ionization chamber when the ionization chamber is at a first polarity;
determining a second change in the capacitance of the ionization chamber when the ionization chamber is at a second polarity;
determining a difference between the first change and the second change; and
using the difference in determining the change in the capacitance of the ionization chamber; and
detecting the presence of smoke by detecting a predetermined change in the capacitance.

2. The method according to claim 1, where the predetermined change in the capacitance is a change in the capacitance within a certain time.

3. The method according to claim 1, where the step of determining the first or second change in the capacitance of the ionization chamber comprises the steps of:
charging the capacitance of the ionization chamber with a first constant current source until a charge on the capacitance is at a first voltage, then discharging the capacitance of the ionization chamber with a second constant current source until the charge on the capacitance of the ionization chamber is at a second voltage, and then repeating charging and discharging the capacitance;
counting the number of times the charge on the capacitance of the ionization chamber is at the first or the second voltage within a certain time period; and
comparing the count numbers of subsequent time periods to determine whether the count number of any one or more of the subsequent time periods has changed by a certain number of counts.

4. A method for detecting smoke using an ionization chamber, wherein the ionization chamber comprises a first ionization chamber open to smoke ingress and a second ionization chamber closed to smoke ingress, the method comprising the steps of:
coupling the ionization chamber to a capacitive sensing module (CSM); and
determining a change in a capacitance of the ionization chamber using the CSM by:
charging the capacitance of a first ionization chamber open to smoke entrance with a first constant current source until a charge on the capacitance of the first ionization chamber is at a first voltage, then discharging the capacitance of the first ionization chamber with a second constant current source until the charge on the capacitance of the first ionization chamber is at a second voltage, and then repeating charging and discharging the capacitance of the first ionization chamber;
counting the number of times the charge on the capacitance of the first ionization chamber is at the first or the second voltage within a certain time period;
charging the capacitance of a second ionization chamber closed to smoke entrance with the first constant current source until a charge on the capacitance of the second ionization chamber is at a first voltage, then discharging the capacitance of the second ionization chamber with the second constant current source until the charge on the capacitance of the second ionization chamber is at the second voltage, and then repeating charging and discharging the capacitance of the second ionization chamber;
counting the number of times the charge on the capacitance of the second ionization chamber is at the first or the second voltage within a certain time period; and
subtracting a count number of the first ionization chamber from a count number of the second ionization chamber and dividing by the count number of the second ionization chamber.

5. The method according to claim 1, where:
in a first measurement, a housing of the ionization chamber is coupled to the CSM; and
in a second measurement, a collector plate of the ionization chamber is coupled to the CSM.

6. The method according to claim 5, further comprising the steps of subtracting a measurement value of the first measurement from a measurement value of the second measurement then dividing by the second measurement value;
and comparing the count numbers of subsequent time periods to determine whether the count number of any one or more of the subsequent time periods has changed by a certain number of counts.

7. The method according to claim 1, further comprising the step of compensating for temperature change with temperature information from a temperature sensor.

8. The method according to claim 1, further comprising the step of compensating for relative humidity change with relative humidity information from a relative humidity sensor.

9. The method according to claim 1, further comprising the step of compensating for voltage change with voltage information from a voltage sensor.

10. An apparatus for detecting smoke, comprising:
an ionization chamber coupled to a capacitive sensing module (CSM) for determining a capacitance of the ionization chamber;
wherein a predetermined change in the capacitance of the ionization chamber indicates the presence of smoke in the ionization chamber; and
circuits for alternately coupling to the ionization chamber at a first polarity for determining a first capacitance of the ionization chamber and coupling to the ionization chamber at a second polarity for determining a second capacitance of the ionization chamber, whereby a difference between the first and second capacitances is used in determining the presence of smoke in the ionization chamber.

11. The apparatus for detecting smoke according to claim 10, wherein the CSM is a peripheral device in a microcontroller.

12. The apparatus for detecting smoke according to claim 11, wherein the microcontroller comprises a digital processor and memory coupled to the CSM and an alarm circuit.

13. The apparatus for detecting smoke according to claim 12, further comprising a temperature sensor coupled to the digital processor and a temperature compensation look-up table stored in the memory coupled to the digital processor and used to compensate temperature induced changes of the capacitance of the ionization chamber.

14. The apparatus for detecting smoke according to claim 12, further comprising a humidity sensor coupled to the digital processor and a humidity compensation look-up table stored in the memory coupled to the digital processor and used to compensate humidity induced changes of the capacitance of the ionization chamber.

15. The apparatus for detecting smoke according to claim 12, further comprising a voltage sensor coupled to the digital processor and a voltage compensation look-up table stored in the memory coupled to the digital processor and used to compensate voltage induced changes of the capacitance of the ionization chamber.

16. The apparatus for detecting smoke according to claim 10, further comprising an audible alert actuated by the presence of smoke in the ionization chamber.

17. The apparatus for detecting smoke according to claim 10, further comprising a visual alert actuated by the presence of smoke in the ionization chamber.

18. The apparatus for detecting smoke according to claim 10, wherein the ionization chamber comprises:
a first ionization chamber open to smoke entrance;
a second ionization chamber closed to smoke entrance;
wherein a predetermined difference in the capacitances of the first and second ionization chambers indicates the presence of smoke in the first ionization chamber.

19. The apparatus for detecting smoke according to claim 10, wherein the CSM is a peripheral device in a microcontroller comprising at least a digital processor and memory coupled to the CSM and an alarm circuit and wherein the ionization chamber comprises:
a first ionization chamber open to smoke entrance;
a second ionization chamber closed to smoke entrance;
wherein a predetermined difference in the capacitances of the first and second ionization chambers indicates the presence of smoke in the first ionization chamber.

* * * * *